(12) United States Patent
Jee et al.

(10) Patent No.: US 7,055,604 B2
(45) Date of Patent: Jun. 6, 2006

(54) USE OF DISTRIBUTED TEMPERATURE SENSORS DURING WELLBORE TREATMENTS

(75) Inventors: Virginia Jee, Sugar Land, TX (US); Nicolas Flamant, Houston, TX (US); Hubertus Thomeer, Houston, TX (US); Sarmad Adnan, Sugar Land, TX (US); Michael Gay, Dickinson, TX (US)

(73) Assignee: Schlumberger Technology Corp., Sugar Land, TX (US)

( * ) Notice: Subject to any disclaimer, the term of this patent is extended or adjusted under 35 U.S.C. 154(b) by 106 days.

(21) Appl. No.: 10/604,515

(22) Filed: Jul. 28, 2003

(65) Prior Publication Data
US 2004/0129418 A1    Jul. 8, 2004

Related U.S. Application Data

(60) Provisional application No. 60/403,865, filed on Aug. 15, 2002.

(51) Int. Cl.
E21B 47/06    (2006.01)
E21B 43/25    (2006.01)

(52) U.S. Cl. .............................. 166/305.1; 166/250.01; 166/312; 73/152.12

(58) Field of Classification Search ............. 166/305.1, 166/312, 250.01; 73/152.11, 152.18, 152.55
See application file for complete search history.

(56) References Cited

U.S. PATENT DOCUMENTS

| 556,669 A | 3/1896 | Frasch |
| RE27,459 E * | 8/1972 | Guinn et al. ............ 166/250.01 |
| 4,324,669 A | 4/1982 | Norman et al. |
| 4,695,389 A | 9/1987 | Kubala |
| 5,054,935 A | 10/1991 | Tanabe et al. |
| 6,271,766 B1 * | 8/2001 | Didden et al. ............ 340/853.1 |
| 6,281,489 B1 * | 8/2001 | Tubel et al. ............ 250/227.14 |
| 6,399,546 B1 | 6/2002 | Chang et al. |
| 6,789,621 B1 * | 9/2004 | Wetzel et al. ............ 166/253.1 |
| 2001/0020675 A1 | 9/2001 | Tubel et al. |
| 2002/0023752 A1 | 2/2002 | Qu et al. |

FOREIGN PATENT DOCUMENTS

GB    2012830    8/1979

OTHER PUBLICATIONS

Temperature Logging by the Distributed Temperature Sensing Technique during Injection Tests by Sakaguchi et al. May 28-Jun. 10, 2000.*
SPE 76747 *Permanent Fiber Optic Monitoring at Northstar: Pressure/Temperature System and Data Overview*—Tor K. Kragas, Bill F. Turnbull and Michael J. Francis.
SPE 71676 *The Use of Fibe-Optic Distributed Temperature Sensing and Remote Hydraulically Operated Interval Control Valves for the Management of Water Production in the Douglas Field*—Michael Tolan, Maurice Boyle and Glynn Williams.
SPE 3505 *Evaluation of Oil Soluble Resin Mixtures as Diverting Agents for Matrix Acidizing*—C.W. Crowe.

(Continued)

*Primary Examiner*—David Bagnell
*Assistant Examiner*—Giovanna M. Collins
(74) *Attorney, Agent, or Firm*—Dave Cate; Tim Curington; Robin Nava

(57) ABSTRACT

The invention relates to a method for treating subterranean formation comprising providing distributed temperature sensors, injecting a treatment fluid and monitoring the temperature across the treatment interval during the injection process.

20 Claims, 2 Drawing Sheets

OTHER PUBLICATIONS

SPE 24781 *A New, Effective Matrix Stimulation Diversion Technique*—Giovanni Paccaloni.
SPE 1977 *Some Applications of Differential Temperature Logging*—Lonnie R. Jameson.
SPE 1750 *Tracing Fluid Movemnets with a New Temperature Technique*—Earl Johns.
SPE 15575 *Foam as a Diverting Technique for Matrix Sandstone Stimulation*—J.W. Burman and B.E. Hall.
SPE 56529 *Case Study of a Novel Acid-Diversion Technique in Carbonate Reservoirs*—F.F. Chang, T. Love, J.B. Blevins III, R.L. Thomas and D. K. Fu.

\* cited by examiner

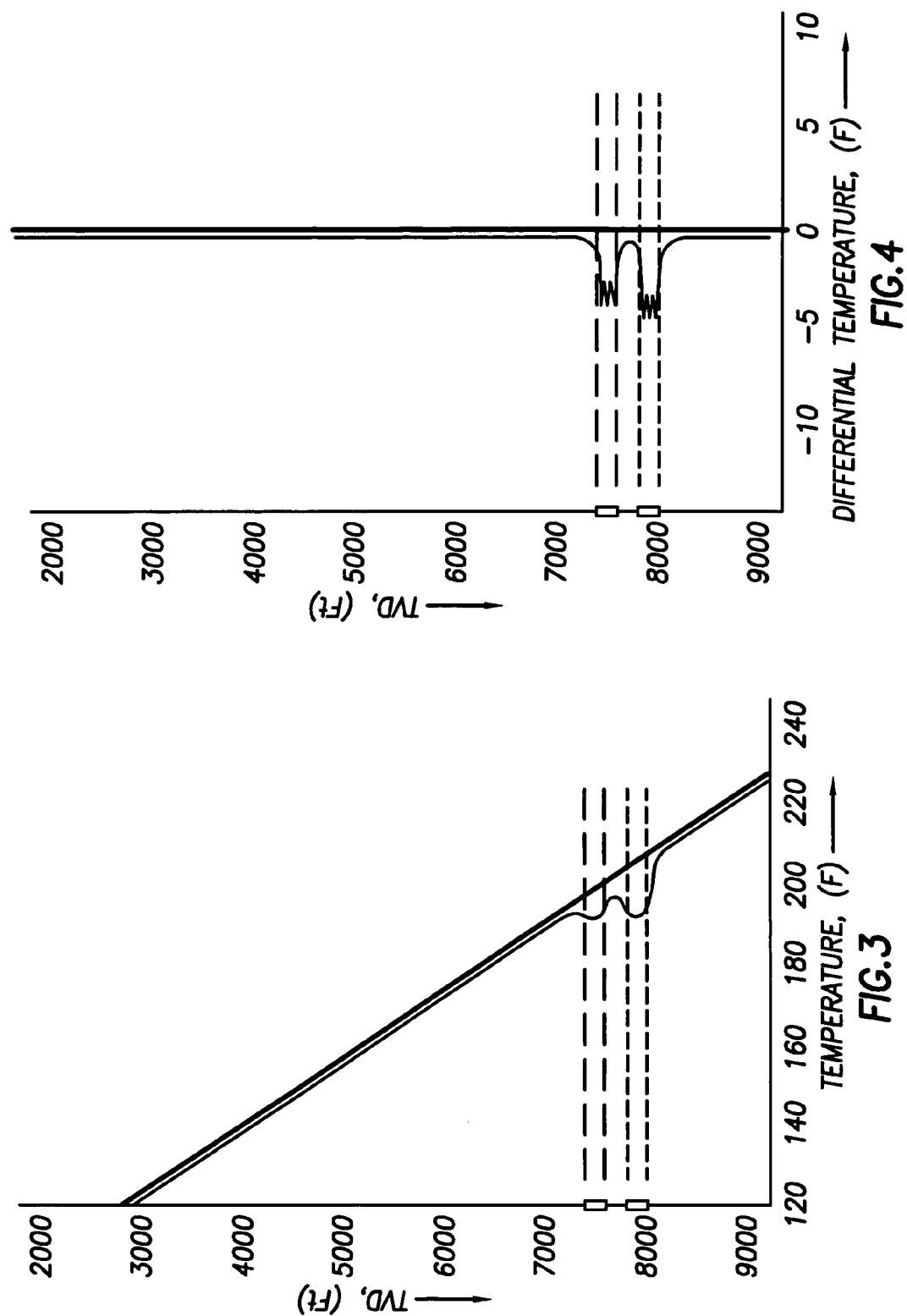

USE OF DISTRIBUTED TEMPERATURE SENSORS DURING WELLBORE TREATMENTS

CROSS REFERENCE TO RELATED APPLICATIONS

This is a Utility Application of prior provisional patent application Ser. No. 60/403,865 filed Aug. 15, 2002 now abandoned.

BACKGROUND OF INVENTION

This Invention is directed to methods for treating hydrocarbon-bearing formations i.e., to increase the production of oil/gas from the formation. More specifically, the invention relates to the placement of fluids for instance for stimulation treatment such as matrix and fracture treatments.

Hydrocarbons (oil, natural gas, etc.) are obtained from a subterranean geologic formation (i.e., a "reservoir") by drilling a well that penetrates the hydrocarbon-bearing formation. This provides a partial flowpath for the oil to reach the surface. In order for oil to be "produced," that is, travel from the formation to the wellbore, and ultimately to the surface, there must be a sufficiently unimpeded flowpath from the formation to the wellbore. If the formation is naturally "tight", i.e. has poorly interconnected pores, or has been damaged by the accumulation of mineral or chemical deposits (scales, precipitates, polymer residues, etc.), resulting from prior treatments or from aging of the reservoir, the flowpath is altered and the production is lower than expected.

Stimulation techniques aim at increasing the net permeability of a reservoir. This is typically achieved through the use of fluid pressure to fracture the formation and/or the injection of chemicals through the wellbore and into the formation to react with and dissolve the deposits or the formation, therefore creating alternative flowpaths. This invention is primarily directed to the latter and thus relates to methods to enhance well productivity by dissolving formation minerals (e.g. calcium carbonate), or deposits by techniques known as "matrix acidizing"and "acid fracturing".

Correct fluid placement plays a critical role in successful well stimulation. Treating fluids must be injected into reservoir zones with lower permeability or higher damage in order to stimulate them. This is true for both matrix acidizing and fracturing. However, injected fluids preferably migrate to higher permeability zones (the path of least resistance) rather than to the lower permeability zones, yet the ones that would most benefit from the treatment.

In response to this problem, numerous, disparate techniques have evolved to achieve more controlled placement of the fluid—i.e., to divert the acid away from naturally high permeability zones and zones already treated, and towards the regions of interest. These techniques can be roughly divided into either mechanical or chemical techniques.

Mechanical techniques include ball sealers (balls dropped into the wellbore and that plug the perforations in the well casing, thus sealing the perforation against fluid entry); packers and bridge plugs, including straddle packers (mechanical devices that plug a portion of the wellbore and thereby inhibit fluid entry into the perforations around that portion of the wellbore); coiled tubing (flexible tubing deployed by a mechanized reel, through which the acid can be delivered to more precise locations within the wellbore); and bullheading or attempting to achieve diversion by pumping the acid at the highest possible pressure—just below the pressure that would actually fracture the formation (described by Paccaloni in SPE 24781).

Chemical diversion techniques can be further divided into ones that chemically modify the wellbore adjacent to portions of the formation for which acid diversion is desired, and ones that modify the acid-containing fluid itself. The first type involve materials that form a reduced-permeability cake on the wellbore face thus reducing the permeability to the acid and diverting it to higher permeability regions. The second type includes foaming agents, emulsifying agents, and gelling agents, which alter the transmissibility of the rock and fluid system.

The primary fluids used in acid treatments are mineral acids such as hydrochloric acid, which was disclosed as the fluid of choice in a patent issued over 100 years ago (U.S. Pat. No. 556,669, Increasing the Flow of Oil Wells, issued to Frasch, H.). At present, hydrochloric acid is still the preferred acid treatment in carbonate formations. For sandstone formations, the preferred fluid is a hydrochloric/hydrofluoric acid mixture. With mineral acids, the major drawback is that they react too quickly and hence penetrate (as unspent acid) into the formation poorly. Second, they are highly corrosive to wellbore tubular components. Organic acids (formic and acetic acid in conventional treatments) are a partial response to the limitations of mineral acids. They are less corrosive and allow greater radial penetration of unspent acid but they also have numerous shortcomings, primarily cost and low reactivity.

Emulsified acid systems and foamed systems are other commercially available responses to the diversion problem, but they are fraught with operational complexity which severely limits their use—e.g., the flow rates of two different fluids, and the bottom hole pressure must be meticulously monitored during treatment.

Gelling agents, especially those not based on crosslinking chemistry but rather upon viscoelastic surfactants, are also used with alternating stages of acid treatment, where the gelling agent preferably decreases the permeability of selected zones and therefore favor the later treatment of the other zones. One system of this type is disclosed in U.S. Pat. No. 4,695,389 (see also, U.S. Pat. No. 4,324,669, and British Patent No. 2,012,830). Another viscoelastic surfactant-based gelling system, also proprietary to Schlumberger, is known as OilSEEKER™, and is disclosed in F. F. Chang, et al., *Case Study of a Novel Acid-Diversion Technique in Carbonate Reservoirs*, SPE 56529, p. 217 (1999).

Self diverting systems, that allow one-step treatment, have also been proposed for instance in U.S. Pat. No. 6,399,546, with a diverter contained within the acid-containing fluid.

These numerous techniques proceed by completely different ways such as modification of the wellbore interface or modification of the acid-containing fluid itself. They are usually very sensitive to any feature in the reservoir that will conduct these diverting agents out of the target zone, for instance a natural fracture and they may actually damage the formation and create rather than solve matrix damages if used improperly. The design of a matrix treatment is consequently very challenging.

Hence, the effectiveness of a treatment, and more particularly the diversion effectiveness, is very difficult to evaluate. During fracture treatments, analysis of surface treating pressures can be used in some cases to analyze it; however, this method does not work for acidizing since pressure surges at the surface may not be correlated to changes in flow profile downhole (see C. W. Crowe, *Evaluation of Oil Soluble Resin*

Mixtures as Diverting Agents for Matrix Acidizing, SPE 3505, 1971 and J. W Burman, B. E. Hall, *Foam as Diverting Technique for Matrix Sandstone Stimulation*, SPE 15575, 1986).

As a result methods for determining actual fluid placement have mainly been limited to post treatment analysis. Some of the methods used have been radioactive tracers, comparison of pre- and post-treatment flowmeter logs, and pre- and post-treatment temperature logs.

One main disadvantage of using post treatment analysis to determine fluid entry is that nothing can be done to change things once the treatment is done. If fluid entry could be monitored during the treatment, changes could possibly be made to the treatment that would change the fluid profile along the wellbore. Therefore, real-time monitoring of fluid entry into the reservoir would be very useful information to have during treatment.

SUMMARY OF INVENTION

This invention provides a new engineering method that enables real-time monitoring of fluid placement, diverter effectiveness, and fracturing parameters during well treatments such as for instance well intervention/stimulation or water control treatments.

The method utilizes distributed temperature sensors so that the temperature vs. position of the fiber can be determined and a temperature profile along the entire fiber becomes available at any time during the treatment, allowing real-time monitoring of the treatment and adjustment is necessary.

According to one aspect of the present invention, the distributed temperature sensors are on an optical fiber through which laser generated light pulses are sent at timed intervals. The return light is analyzed and information, such as temperature and pressure vs. position on the fiber can be determined.

According to another aspect of the present invention, an array of Fiber Bragg Grating temperature sensors is used, In this later case, a continuous light source is used and the measurement is based on wavelength interrogation.

The fiber is preferably positioned in the well utilizing coiled tubing but may be also positioned through other positioning tools such as tubing, wireline tool. The fiber may be simply injected bare or coated with a composite or a metal coating.

The deployment is preferably carried out while rigging up for the service and is removed at the completion of the service.

Comparison of temperature profiles through the treatment zone at various times during the treatment, for example after an acid stage exits the end of the coiled tubing, can be used to determine where the fluid stage entered the formation. Since the temperature of most treating fluids will be cooler than the bottomhole temperature, a cooling effect from fluid entry should be visible. In some cases, it may also be possible to see heating of the reservoir due to the exothermic reaction of the acid with the rock. Monitoring of the pressure also provides information that will assist in treatment evaluation.

According to a preferred embodiment, the pressure is also monitored through the treatment interval during fracturing. Distributed pressure sensors may also be used. This allows for instance real-time diagnosis of imminent screenout or emerging fracture geometry. It also permits the on-site engineer to monitor fracture evolution and make adjustments to ensure tip-screen-out in high permeability zones.

BRIEF DESCRIPTION OF DRAWINGS

FIG. 3 shows the temperature gradient after injecting a second treatment stage;

FIG. 4 shows the differential temperature trace.

DETAILED DESCRIPTION

Figure 2:
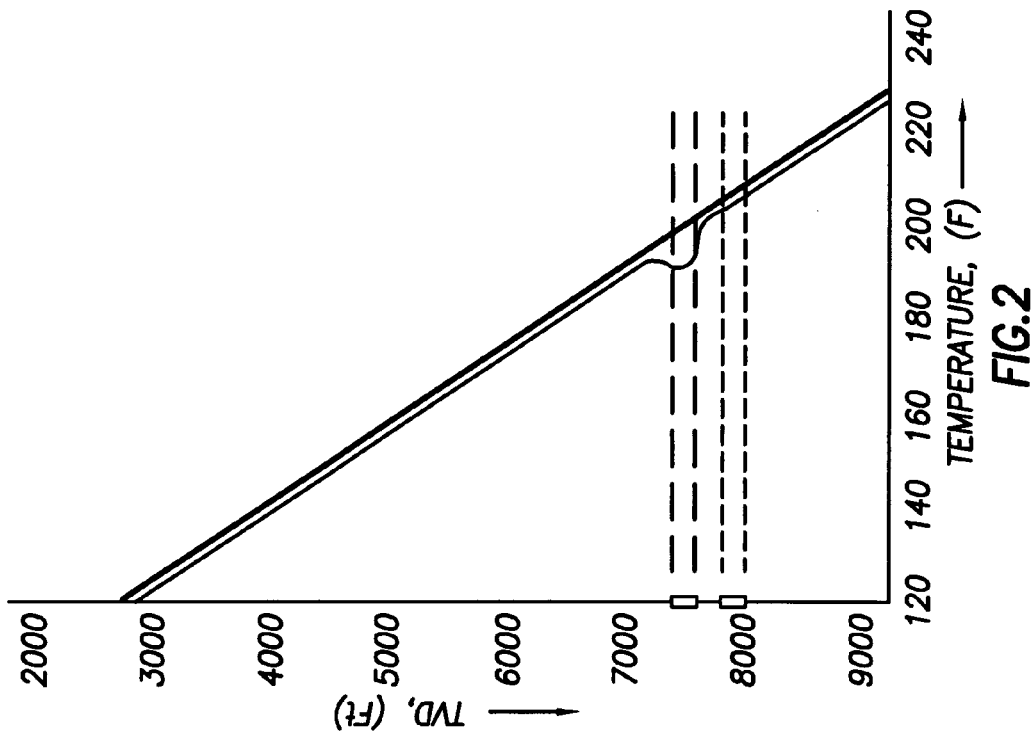
FIG. 2 shows the temperature gradient after the injection of a first treatment stage.

Analysis of differential temperature logs has been used in the oil and gas industry since the late 1960's as related in SPE 1750—*Tracing Fluid Movements with a New Temperature Technique*, E. Johns, 1967 and SPE 1977—*Some Applications of Differential Temperature Logging*, L. R. Jameson. However, this method is rarely used, possibly because it requires well logging both before and after the treatment. Today, a more typical method of determining fluid entry is the use of radioactive (RA) tracers.

The distributed temperature sensing (DTS) technology was pioneered in the early 1980's. It is based on optical time-domain reflectometry (OTDR), which is used extensively in telecommunications cable testing. Application in the oil and gas industry to date has been as permanent installations (see SPE 71676—The Use of Fiber-Optic Distributed Temperature Sensing and Remote Hydraulically Operated Interval Control Valves for the Management of Water Production in the Douglas Field, M. Tolan, M. Boyle, G. Williams, 2001 and SPE 76747—Permanent Fiber Optic Monitoring at Northstar: Pressure/Tempearture System and Data Overview, T. K. Kragas, B. F. Turnbull, M. J. Francis, 2002). OTDR technology sends short duration light pulses down the fiber optic cable and measures the arrival time and magnitude of the returning backscattered light to determine the location and type of faults in the cable. The backscattered light is generated by changes in density and composition as well as molecular and bulk vibrations.

Generally, pulses of light at a fixed wavelength are transmitted from a light source in surface equipment down a fiber optic line. At every measurement point in the line, light is back-scattered and returns to the surface equipment. Knowing the speed of light and the moment of arrival of the return signal enables its point of origin along the fiber line to be determined. Temperature stimulates the energy levels of the silica molecules in the fiber line. The back-scattered light contains upshifted and downshifted wavebands (such as the Stokes Raman and Anti-Stokes Raman portions of the back-scattered spectrum), which can be analyzed to determine the temperature at origin. In this way the temperature of each of the responding measurement points in the fiber line can be calculated by the equipment, providing a complete temperature profile along the length of the fiber line. This general fiber optic distributed temperature system and technique is known in the prior art. As further known in the art, it should be noted that the fiber optic line may also have a surface return line so that the entire line has a U-shape. One of the benefits of the return line is that it may provide enhanced performance and increased spatial resolution to the temperature sensor system.

DTS is used to detect water or gas influx, to monitor thermal EOR projects, and to monitor gas lift valves. It has been used with coiled tubing in the same way as the permanent installations.

This invention focuses on the use of fiber optic measurements during well intervention treatments. The fiber optic line is deployed at the time of service and removed after the completion of service. Distributed temperature measurements will be used to monitor where the treating fluids enter the formation. Fluid placement is a variable that is typically only inferred by pressure changes during a treatment. The ability to monitor fluid placement during the treatment will give stimulation engineers information that will allow them to make adjustments to obtain better injection profiles. This is especially true in matrix acid jobs where the goal may be to inject the treating fluid into zones that initially take fluid poorly.

An example procedure for use in acid treatments would work as follows:

The optical fiber is positioned in the well with its end at or slightly below the reservoir The fiber is allowed to equilibrate until a baseline temperature profile is determined for the well across the treatment interval.

Since temperature is available at all depths at all times, a differential profile can be calculated by subtracting the temperature at each depth at the desired time from the temperature at depth at the baseline time. Positive changes would indicate heating (may be possible due to chemical reactions) and negative changes would indicate cooling (due to cooler fluids being injected).

Pump an injectivity test with a non-reactive fluid, such as brine. The differential profile should be calculated and evaluated before pumping the treatment in case an initial diverter stage is determined to be necessary. The brine will cool down the formation where it gets in contact with it. The change in temperature will indicate the areas open to flow. Combining the measurements with a temperature simulation of the injection will further the analysis and indicate the volume of fluids that have gone into each zone, thus providing the injectivities of each zone.

Pump a complete treatment stage and diverter. A treatment stage can be a single fluid or multiple fluids depending on the type of treatment being pumped and the reservoir being treated. Carbonates are typically treated with a single fluid, such as HCl. Sandstones typically have a 3 fluid treatment stage, preflush, main fluid, and overflush, before the diverter is pumped.

Shut down until the temperature stabilizes and a sufficient temperature differential is seen. Expected shut in time will vary depending on the reservoir properties and fluids pumped but should be on the order of minutes. Expected shut in time should not be greater than an hour.

Continue pumping the treatment, shutting in for fluid entry analysis after each diverter stage (as a minimum).

During the shut in, the temperature deviation from both the baseline and the temperature profile measured prior to the shut in are monitored continuously. The derivatives relative to time of those two curves are also calculated. The differences in cooling times and rates of cooling along the wellbore indicate in which layer of the reservoir the treatment fluid or diverter stage has gone. Performing a temperature simulation of the injection and matching the results of the simulation with the measurements will further the analysis and indicate the volume of fluids that have gone into each zone.

Differential temperature profiles should be calculated after each diverter stage and at the end of the first stage to follow the diverter to determine if the diverter is working. After diversion, the fluid should move to a different zone. If this does not occur, additional diverter may be required and the real-time monitoring allows real-time adjustment of the amount of diverter. Where coiled tubing is used, the temperature profile may also show that its position is not optimized and the treatment may be adjusted by changing the position of the coiled tubing injection point.

The analysis can be extended through the use of a coupled wellbore/reservoir temperature model. Combining the measured temperature with a temperature simulation of the injection can provide a method to indicate the individual zone injectivity. Performing a temperature simulation of the injection and matching the results of the simulation with the measurements can be used to determine the volume of fluids that have gone into each zone.

Determining the actual position of the injection is also valuable information. Post-treatment spinner logs can be used to assess where the fluid went, but then it is too late to change that injection profile. Real-time knowledge of where the diverter is going, may trigger the decision of re-positioning the coiled tubing to inject away from that zone and into the next zone that needs treatment. Knowing the "where" of actual treatment will help the operator in managing conformance in standard and gravel pack completions.

Managing conformance means ensuring the treatment goes into the zones that have the most production potential to optimize reservoir draining. For instance, in secondary and tertiary recovery projects the goal is to maximize injection and sweep of unswept zones. With gravel packing treating, it is suitable to make sure treatments are uniform so you will not "overtreat" any particular section of the pack which could lead to gravel pack failure The main difference between the current method and past methods is that the distributed temperature sensing technology makes the temperature profile across the interval available at all times. Therefore calculation of the differential temperature profile can be done without making logging passes or moving the CT. It should also be possible to program the final data acquisition software to generate the differential profile at any time during the treatment upon command. This would make real-time fluid entry evaluation not only possible but easy to do.

Modifications of this basic procedure would have to be developed if foam diversion is used or if nitrified fluids are pumped. Availability of pressure at depth will allow much better evaluation of foam diversion because downhole foam quality can be more accurately estimated. It may also be possible to monitor foam degradation.

Real-time bottomhole pressure (BHP) through the use of optical fiber will also be very useful in hydraulic fracturing treatments. BHP is essential for determining accurate closure pressure and accurate pressure response during the fracturing treatment allows the on-site engineer to diagnose any imminent screenout and promptly go to flush to avoid time-consuming and potentially costly cleanout if screenout occurs. BHP also provides the engineers the data needed to design and monitor tip-screen-out treatment in high permeability formation and to use the fracturing software to perform post-job pressure match and optimize the future treatment design.

CoilFRAC is an especially cost-effective way to stimulate multiple zones in a single pipe trip. Since straddle packers are used for CoilFRAC, there is no way to obtain true BHP by simply measuring the annulus pressure. The BHP calculated from the surface pressure is highly inaccurate due to high friction through the coiled tubing and the CoilFRAC bottom hole assembly (BHA). Optical fiber installed inside the BHA and below the fracturing port can provide a direct measurement of the BHP.

Measurement of temperature profile can also be used to determine fracture height after a fracture treatment. The formation adjacent to the fracture will exhibit more cooling than the rock above and below. Therefore, the temperature profile along depth and its change with time provides the indication of fracture growth and the final height. The fracture height measurement tells the engineer whether the fracture is properly placed in the target zones and whether the fracture could propagate into water or gas zones, which are to be avoided. Based on the information, fracture design can be adjusted to achieve optimal well productivity.

Figure 1:
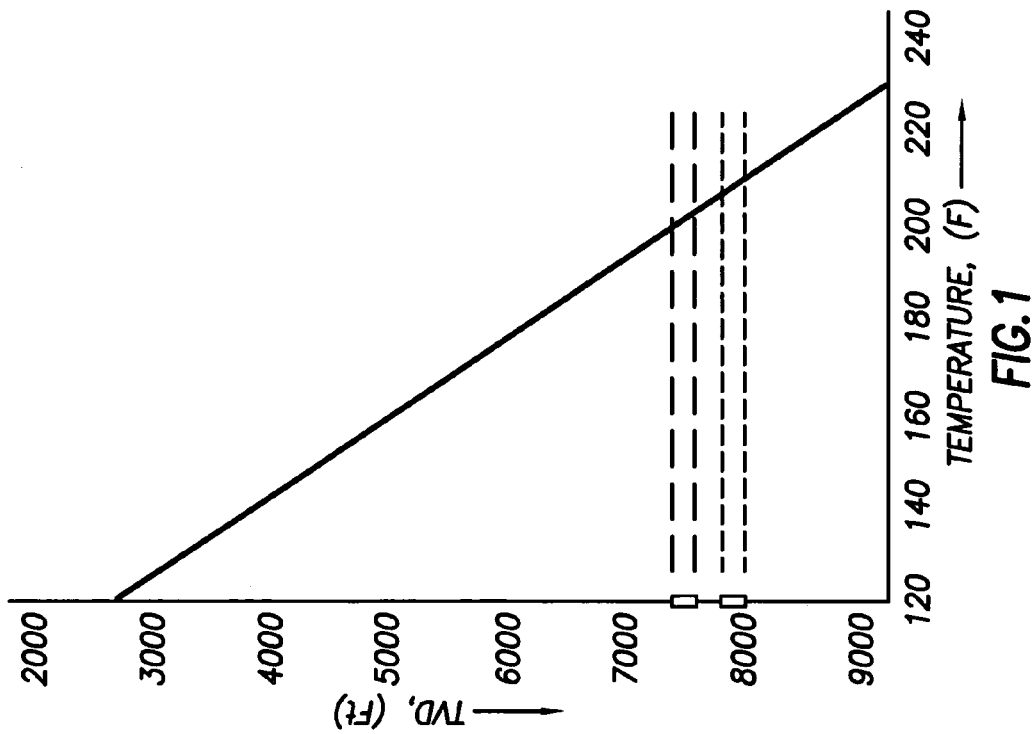
FIG. 1 shows the baseline temperature gradient in a well, as a function of the true vertical depth.

Example data shown in the figures is synthetic and represent idealized results. FIG. 1 illustrates the baseline temperature gradient measured after attaining stabilized temperature gradient with the fiber optic positioned across the reservoir before starting the treatment. The temperature (hereby expressed in degrees Fahrenheit) depends linearly of the TVD (true vertical depth), hereby expressed in feet. The dashed lines between about 7500 feet and 8000 feet indicate the position of perforations.

FIG. 2 shows the stabilized temperature gradient for the same well after the first treatment stage. In this case, the treatment induces a diminution of the temperature in the perforation zone (compare to the baseline curve repeated for reference purposes).

After a second treatment stage, the stabilized gradient further evolves (see FIG. 3). The differential curve calculated at the end of the job, FIG. 4, shows clearly in this example that the treatment has entered both zones, thereby proving the effectiveness of the diverter.

The invention claimed is:

1. A method for treating a drilled well, the method comprising the steps of:
    positioning distributed temperature sensors on a fiber along an interval within a well, wherein the distributed temperature sensors provide substantially continuous temperature monitoring along the interval;
    obtaining a baseline temperature profile across the interval;
    monitoring substantially continuously the temperature along the interval;
    calculating a differential temperature profile across the interval relative to the baseline temperature profile;
    injecting a fluid into the well and into one or more zones surrounding the interval;
    shutting-in the well until the temperature in the well substantially stabilizes;
    monitoring the shut-in temperature along the interval during the shut-in period;
    determining the shut-in temperature deviation relative to the baseline temperature profile across the interval; and
    determining the one or more formation zones in which the injected fluid flowed.

2. The method of claim 1, further comprising the step of determining the shut-in temperature deviation relative to the differential temperature profile measured prior to the shut-in.

3. The method of claim 1, further comprising the step of determining the volume of the fluid injected into the one or more zones.

4. The method of claim 1, wherein the fiber has a bottom end including a temperature sensor for substantially continuous monitoring of bottom-hole temperature.

5. The method of claim 1, wherein the fiber has a bottom end, the bottom end including a temperature sensor for substantially continuous monitoring of bottom-hole temperature and a pressure sensor for measuring for substantially continuous monitoring of bottom-hole pressure.

6. The method of claim 1, wherein the fiber has a bottom end including a pressure sensor for substantially continuous monitoring of bottom-hole pressure.

7. The method of claim 1, further including the step of injecting a subsequent fluid pursuant to the step of determining the zone of injection of the prior injected fluid.

8. The method of claim 1, further including the steps of:
    injecting a diverter into the well pursuant to the step of determining the zone of injection of the prior injected fluid; and
    injecting a subsequent fluid pursuant to the step of determining the zone of injection of the prior injected fluid.

9. The method of claim 1, wherein the fluid is a matrix treatment agent.

10. The method of claim 1, wherein the fluid is a matrix acidizing agent.

11. The method of claim 1, wherein the fluid is a fracturing agent.

12. The method of claim 1, wherein the fluid is an acid fracturing agent.

13. The method of claim 1, wherein the fluid is a gravel packing agent.

14. A method for treating a drilled well, the method comprising the steps of:
    positioning distributed temperature sensors on a fiber along an interval within a well surrounded by one or more formation zones, wherein the distributed temperature sensors provide substantially continuously temperature monitoring along the interval;
    obtaining a baseline temperature profile across the interval;
    monitoring substantially continuously the temperature along the interval;
    calculating a differential temperature profile across the interval relative to the baseline temperature profile;
    injecting a fluid non-reactive with the one or more formation zones into the well and the one or more formation zones;
    calculating the injectivity of the one or more formation zones based on temperature profile along the interval during the step of injecting the non-reactive fluid;
    injecting a fluid reactive to the one or more formation zones into the well and into one or more formation zones surrounding the interval pursuant to the calculating the injectivity step;
    shutting-in the well until the temperature in the well substantially stabilizes;
    monitoring the shut-in temperature along the interval during the shut-in period;
    determining the shut-in temperature deviation relative to the baseline temperature profile across the interval; and
    determining the one or mare formation zones in which the injected fluid flowed.

15. The method of claim 14, further comprising the step of determining the shut-in temperature deviation relative to the differential temperature profile measured prior to the shut-in.

16. The method of claim 14, further including the step of injecting a diverter into the well pursuant to the step of determining the injectivity of the one or more formation zones relative to the injecting of the non-reactive fluid.

17. The method of claim 14, further comprising the step of determining the volume of the reactive fluid injected into the one or more zones.

18. The method of claim 14, further including the step of injecting a subsequent fluid pursuant to the step of determining the zone of injection of the prior injected fluid.

19. The method of claim 14, further including the steps of:
   injecting a diverter into the well pursuant to the step of determining the zone of injection of the prior injected fluid; and
   injecting a subsequent fluid pursuant to the step of determining the zone of injection of the prior injected fluid.

20. The method of claim 14, further including the steps of:
   injecting a diverter into the well pursuant to the step of determining the one or more formation zones of injection of the prior injected reactive fluid; and
   injecting a subsequent fluid pursuant to the step of determining the zone of injection of the prior injected reactive fluid.

* * * * *